(12) United States Patent
Nguyen

(10) Patent No.: US 7,464,709 B2
(45) Date of Patent: Dec. 16, 2008

(54) INTEGRATED REGULATOR MOUNT FOR A VENTILATOR SYSTEM

(75) Inventor: Tom Thong Nguyen, Highlands Ranch, CO (US)

(73) Assignee: Norgren, Inc., Littleton, CO (US)

( * ) Notice: Subject to any disclaimer, the term of this patent is extended or adjusted under 35 U.S.C. 154(b) by 611 days.

(21) Appl. No.: 11/147,551

(22) Filed: Jun. 8, 2005

(65) Prior Publication Data
US 2006/0278226 A1   Dec. 14, 2006

(51) Int. Cl.
*A61M 16/00*   (2006.01)

(52) U.S. Cl. ............. 128/205.24; 128/204.18; 128/205.11

(58) Field of Classification Search ............ 128/205.24, 128/204.18, 205.11; 137/505, 507, 315.11, 137/454.5
See application file for complete search history.

(56) References Cited

U.S. PATENT DOCUMENTS

| | | | |
|---|---|---|---|
| 3,229,716 A * | 1/1966 | Johnson et al. ............ | 137/588 |
| 3,240,223 A | 3/1966 | Vander Horst | |
| 3,756,229 A * | 9/1973 | Ollivier ................ | 128/204.26 |
| 3,820,539 A * | 6/1974 | Ollivier ................ | 128/203.12 |
| 3,842,828 A * | 10/1974 | Bird ..................... | 128/200.14 |
| 3,985,131 A * | 10/1976 | Buck et al. ............ | 128/204.23 |
| 4,044,763 A * | 8/1977 | Bird ..................... | 128/204.26 |
| 4,121,579 A * | 10/1978 | Bird ..................... | 128/204.25 |
| 4,442,856 A * | 4/1984 | Betz ........................ | 137/98 |
| 4,592,349 A * | 6/1986 | Bird ..................... | 128/204.25 |
| 5,727,588 A | 3/1998 | Lin | |
| 5,755,254 A * | 5/1998 | Carter et al. ............ | 137/340 |
| 6,722,388 B1 * | 4/2004 | McAden ................ | 137/454.5 |

FOREIGN PATENT DOCUMENTS

| | | |
|---|---|---|
| DE | 10 90 478 B | 10/1960 |
| EP | 0 032 979 A1 | 8/1981 |
| EP | 0296 809 A | 12/1988 |
| GB | 2 099 110 A | 12/1982 |

OTHER PUBLICATIONS

"840tm Ventilator System" http://www.puritanbennett.com/prod/Product.aspx?S1=VEN&S2=VNT&id=202, obtained Apr. 15, 2005, pp. 1-2.

* cited by examiner

*Primary Examiner*—Steven O Douglas
(74) *Attorney, Agent, or Firm*—The Ollila Law Group LLC

(57) ABSTRACT

An integrated regulator mount for a ventilator is disclosed. The ventilator has the regulator mount built into a manifold. The regulator mount is formed into the manifold on two opposite faces. One face is configured to mount the valve seat for the regulator. The valve spring assembly is held against the valve seat by a valve spring retaining plug mounted in the manifold. The regulator case and diaphragm assembly mount on the opposite face of the manifold.

6 Claims, 19 Drawing Sheets

INTEGRATED REGULATOR MOUNT FOR A VENTILATOR SYSTEM

RELATED APPLICATIONS

This application is related to applications "SYSTEM AND METHOD TO PREVENT THE IMPROPER INSTALLATION OF THE INLET FITTINGS IN A VENTILATOR SYSTEM," having application Ser. No. 11/147,751, "PNEUMATIC SHUTTLE VALVE FOR A VENTILATOR SYSTEM," having application Ser. No. 11/148,045, "VENTILATOR SYSTEM," having application Ser. No. 11/147,553, "INTEGRATED MANIFOLD FOR A VENTILATOR SYSTEM," having application Ser. No. 11/148,042, and "MANIFOLD ASSEMBLY FOR A VENTILATOR SYSTEM" having application Ser. No. 11/147,560, filed on the same day as this application and included by reference into this application.

BACKGROUND OF THE INVENTION

1. Field of the Invention

The invention is related to the field of heath care products, and in particular, to a portable ventilator system.

2. Description of the Prior Art

Ventilator systems typically combine a high pressure oxygen flow with a compressed air flow to form a controlled ratio low pressure flow suitable for delivery into a patient's lungs. A regulator is used to reduce the pressure of a high pressure oxygen source to a controlled output pressure. The regulator is configured to accept a wide range of input pressures from the oxygen source and produce a constant low pressure, variable flow, output source. Typically the high pressure oxygen is passed through a filtering system before being introduced into the regulator. A second regulator is used to reduce the pressure of a compressed air source to the same controlled output pressure as the oxygen regulator. Typically the compressed air is passed through a separate filtering system before being introduced into the second regulator. Once the pressures of the oxygen and air have been reduced, the two flows are mixed together in a controlled ratio and delivered to a patient. The ratio of oxygen to air is typically a programmable ratio and can be set anywhere between 100% oxygen 0% air, to 0% oxygen 100% air.

The high pressure oxygen source may be bottled oxygen or may come from a hospital wall supply. Both types of oxygen sources typically connect to the same fitting on the ventilator system. The compressed air source may be a built in air compressor or may use a hospital compressed air wall supply. The two types of compressed air typically connect to different fittings on the ventilator system. There is typically a system of check valves or switching valves that allow the compressed air supply to be changed from the hospital wall source to the air compressor during use by a patient. Currently, ventilator systems connect the filters, regulators, and check valves through a number of different pipes and fittings. Unfortunately, each joint in the series of pipes and fittings is a potential place for a leak. Because oxygen is highly combustible, any leak can be a danger to the patient or the heath care provider. The complex gas passageways may be costly to produce and may produce pressure drops due to the many flow restrictions.

Today's ventilator systems may also have a number of usability problems. Many of the ventilator systems used today have the oxygen and compressed air connections in difficult to use locations, for example underneath the unit and partially enclosed. This makes it difficult for the heath care provider to connect the oxygen and air supply to the ventilator. The air and oxygen filters typically have replaceable components. In many of today's ventilators, the two filters are located in different areas on the unit and may be difficult to access.

Therefore there is a need for an improved ventilator system.

SUMMARY OF THE INVENTION

An integrated regulator mount for a ventilator is disclosed. The ventilator has the regulator mount built into a manifold. The regulator mount is formed into the manifold on two opposite faces. One face is configured to mount the valve seat for the regulator. The valve spring assembly is held against the valve seat by a valve spring retaining plug mounted in the manifold. The regulator case and diaphragm assembly mount on the opposite face of the manifold.

DETAILED DESCRIPTION OF THE PREFERRED EMBODIMENT

FIGS. 1-20 and the following description depict specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

Figure 1:
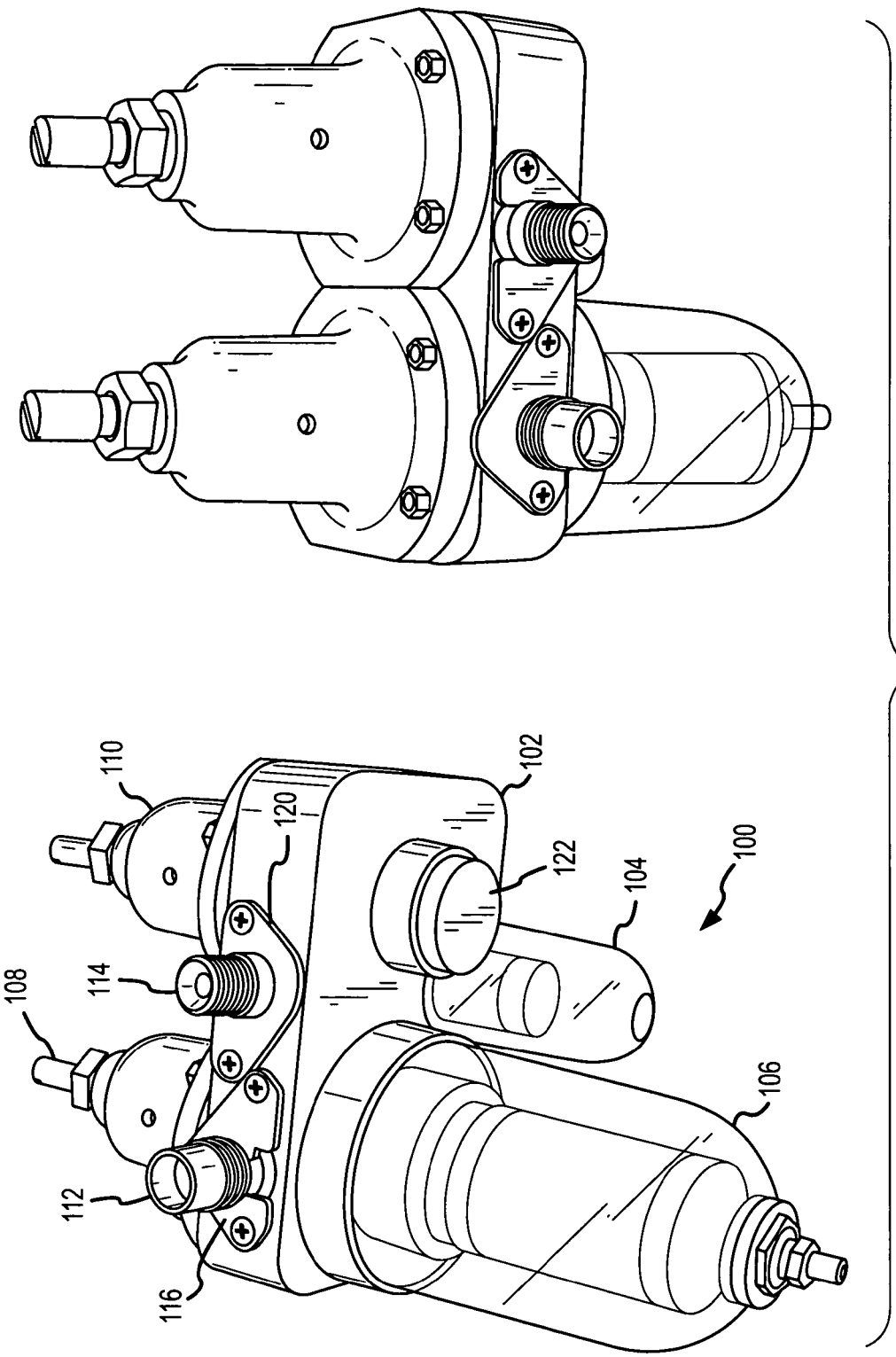
FIG. 1 is an isometric view of the back side of an integrated manifold assembly 100 in one example embodiment of the invention.

FIG. 1 is an isometric view of the back side of a manifold assembly 100 in one example embodiment of the invention. Manifold assembly 100 comprises manifold 102, oxygen filter 104, compressed air filter 106, compressed air regulator 108, oxygen regulator 110, compressed air outlet fixture 112, oxygen outlet fixture 114, horse shoe clips 116 and 120, and plug 122.

In operation a high pressure oxygen source (not shown) is connected to an oxygen inlet fixture (not shown) mounted on the front side of the manifold 102. The high pressure oxygen typically comes from either an in wall oxygen source or an oxygen tank. The high pressure oxygen passes through oxygen filter 104 and then is directed to oxygen regulator 110. Oxygen filter 104 is mounted on the bottom face of manifold 102. Oxygen regulator 110 is configured to accept a wide range of input pressures from the oxygen source and produce a constant low pressure, variable flow, oxygen output. Oxygen regulator 110 is mounted on the top side of manifold 102. The low pressure flow from oxygen regulator 110 exits the integrated manifold assembly 100 through oxygen outlet connector 114 mounted on the back side of manifold 102. A compressed air source (not shown) is connected to a compressed air inlet fixture (not shown) mounted on the front side of the manifold 102. The compressed air typically comes from an in wall compressed air source. The compressed air passes through compressed air filter 106 and then is directed to compressed air regulator 108. Compressed air filter 106 is mounted on the bottom face of manifold 102 and is a different diameter than oxygen filter 104. Compressed air regulator 108 is configured to accept a wide range of input pressures from the compressed air source and produce a constant low pressure, variable flow, air output. Compressed air regulator 108 is mounted on the top side of manifold 102. The low pressure flow from compressed air regulator 108 exits the integrated manifold assembly 100 through compressed air outlet connector 112 mounted on the back side of manifold 102. In one example embodiment of the invention, compressed air regulator 108 and oxygen regulator 110 are essentially identical.

Figure 2:
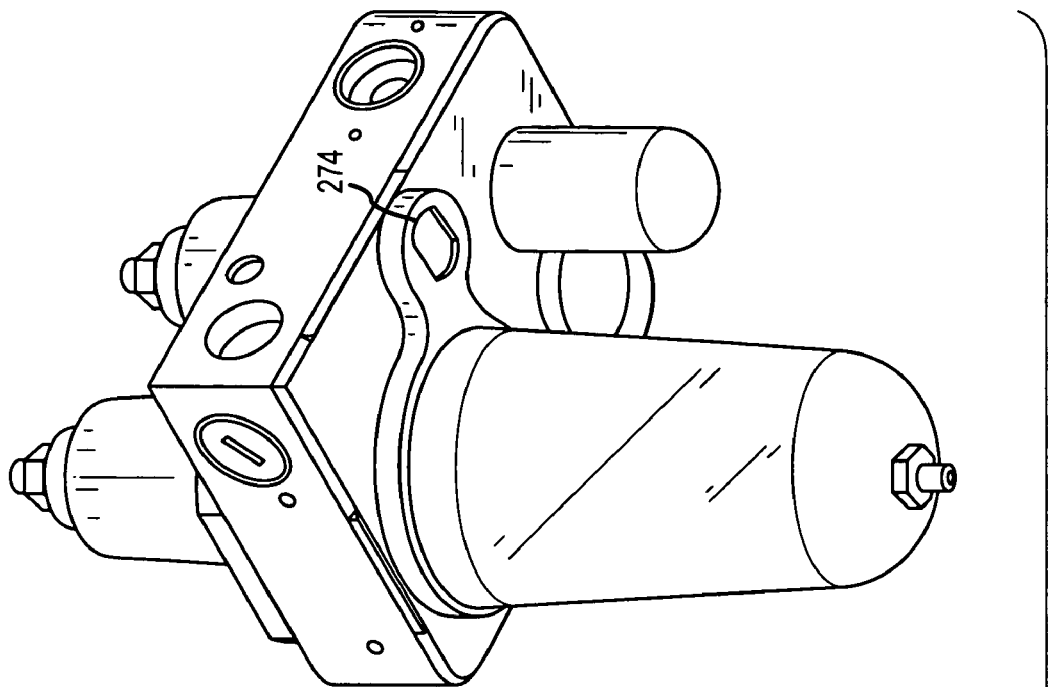
FIG. 2 is an isometric view of the front of an integrated manifold assembly 200 in one example embodiment of the invention.
Figure 2:
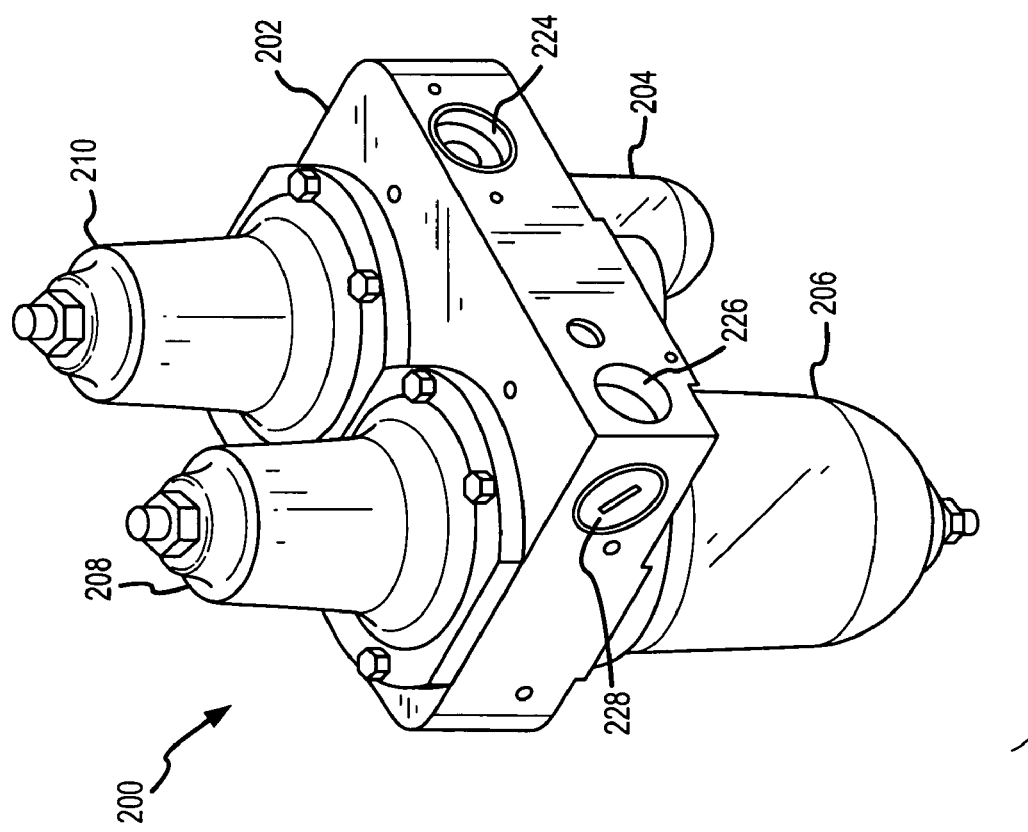

FIG. 2 is an isometric view of the front of a manifold assembly 200 in one example embodiment of the invention. Manifold assembly 200 comprises manifold 202, oxygen filter 204, compressed air filter 206, compressed air regulator 208, oxygen regulator 210, compressed air inlet opening 226, oxygen inlet opening 224, compressor inlet opening 274, and shuttle plug cap 228.

In operation, a compressed air source (not shown) is connected to compressed air inlet opening 226 on the front side of the manifold 202. The compressed air passes through compressed air filter 206 and then is directed to compressed air regulator 208. A compressor (not shown) can also be used as the compressed air source. When using a compressor as the compressed air source, the compressor is connected to the manifold using compressor inlet opening 274. A pneumatic shuttle valve is configured to switch between the compressed air inlet fixture and the compressor inlet fixture, dependent on which fixture is being used as the air source.

Figure 3A:
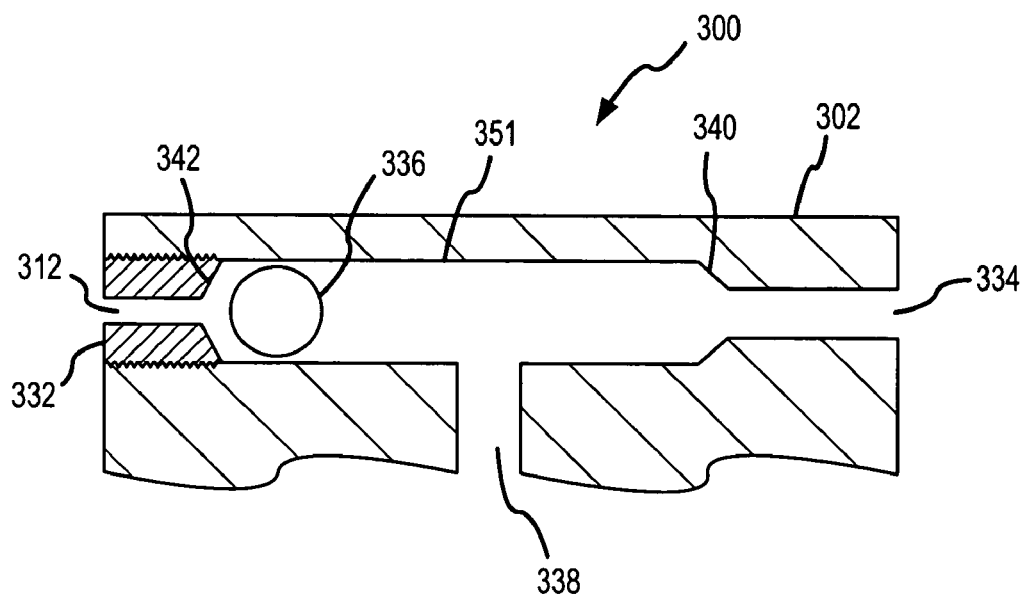
FIG. 3a is a cutaway view of a pneumatic shuttle valve in one example embodiment of the invention.

FIG. 3a is a cutaway view of a pneumatic shuttle valve in one example embodiment of the invention. In one example embodiment of the invention, pneumatic shuttle valve 300 may be formed into manifold 302. Pneumatic shuttle valve 300 comprises manifold 302, shuttle plug cap 332, and shuttle plug 336. Manifold 302 forms a shuttle valve passageway 351, a first inlet opening 334 and first sealing surface 340. Shuttle plug cap 332, threaded into manifold 302, forms a second inlet opening 312 and a second sealing surface 342. Manifold 302 also forms outlet opening 338. In one example embodiment of the invention, there may be an O-ring or gasket used to form a seal between shuttle plug cap 332 and manifold 302.

Figure 3B:
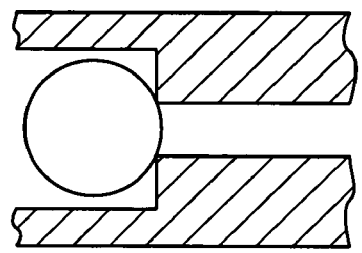
FIG. 3b is a cutaway view of a pneumatic shuttle valve with a straight shouldered shape in one example embodiment of the invention.
Figure 3C:
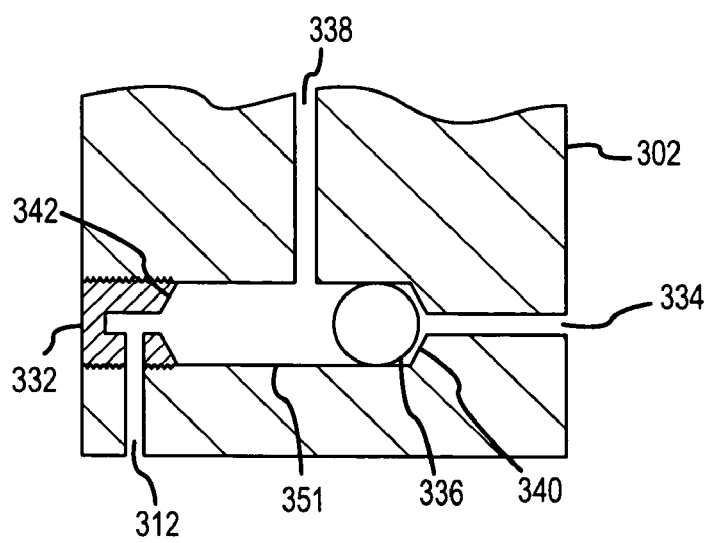
FIG. 3c is a cutaway view of a shuttle valve in another example embodiment of the invention.

In operation, when a compressed air source or other high pressure gas is attached to inlet opening 334 and there is nothing attached to inlet opening 312, the high pressure air entering inlet opening 334 forces shuttle plug 336 against sealing surface 342 in shuttle plug cap 332 preventing flow through inlet opening 312. With shuttle plug 336 forced against sealing surface 342 the high pressure air from inlet opening 334 is forced into outlet opening 338. When a compressed air source is attached to inlet opening 312 and there is nothing attached to inlet opening 334, the high pressure air entering inlet opening 312 forces shuttle plug 336 against sealing surface 340 formed in manifold 302, preventing flow through inlet opening 334. With shuttle plug 336 forced against sealing surface 340 the high pressure air from inlet opening 312 is forced into outlet opening 338. When both inlet openings have an air supply attached to them, the pneumatic shuttle valve will seal the inlet opening to the source having the lowest amount of pressure. FIG. 3a and 3c shows the sealing surfaces 340 and 342 as conical surfaces. Other shapes may be use, for example a spherical shape, a straight shouldered shape, or the like. FIG. 3b is a cutaway view of a pneumatic shuttle valve with a straight shouldered shape in one example embodiment of the invention.

Figure 19:
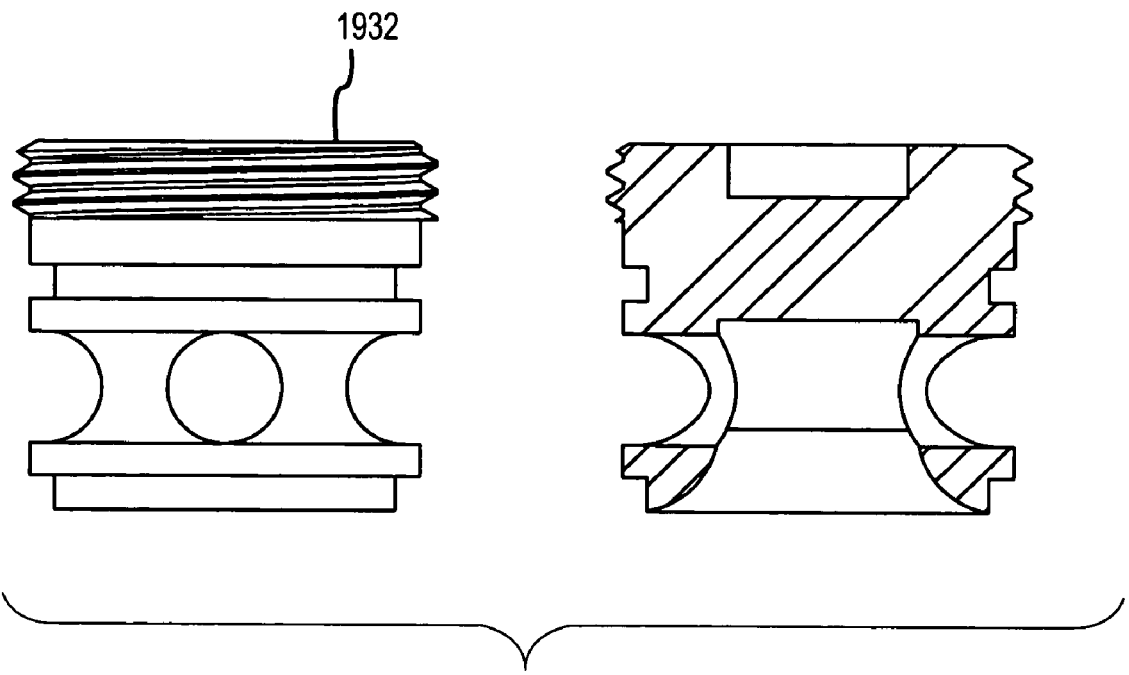
FIG. 19 is a drawing of shuttle plug cap 1932 in an example embodiment of the invention.

FIG. 3c is a sectional view of a shuttle valve in another example embodiment of the invention. FIG. 3c comprises manifold 302, shuttle plug cap 332, and shuttle plug 336. In the example embodiment shown in FIG. 3c, both inlet openings (312 and 334) are formed into manifold 302. Inlet opening 312 passes through the shuttle plug cap. Inlet opening 312 enters the side of shuttle plug cap 332 and exits from the end of shuttle plug cap. The shuttle plug cap shown in FIG. 3c performs a number of different functions. the shuttle plug cap forms sealing surface 342, allows access for shuttle plug 336 to be inserted into the shuttle valve passageway 351, forms part of one of the inlet opening 312, and seals the shuttle valve passageway 351. FIG. 19 is a drawing of shuttle plug cap 1932 in an example embodiment of the invention.

FIGS. 3a, 3b and 3c show shuttle plug 336 as a spherical shape, but shuttle plug may be formed into other shapes, for example a cylindrical shape with conical ends. Any combination of shapes can be used between sealing surfaces 340 and 342 and the corresponding shuttle plug shape, as long as the shuttle plug forms a seal against the sealing surface when the shuttle plug is forced against the sealing surface by the high pressure gas.

Figure 4:
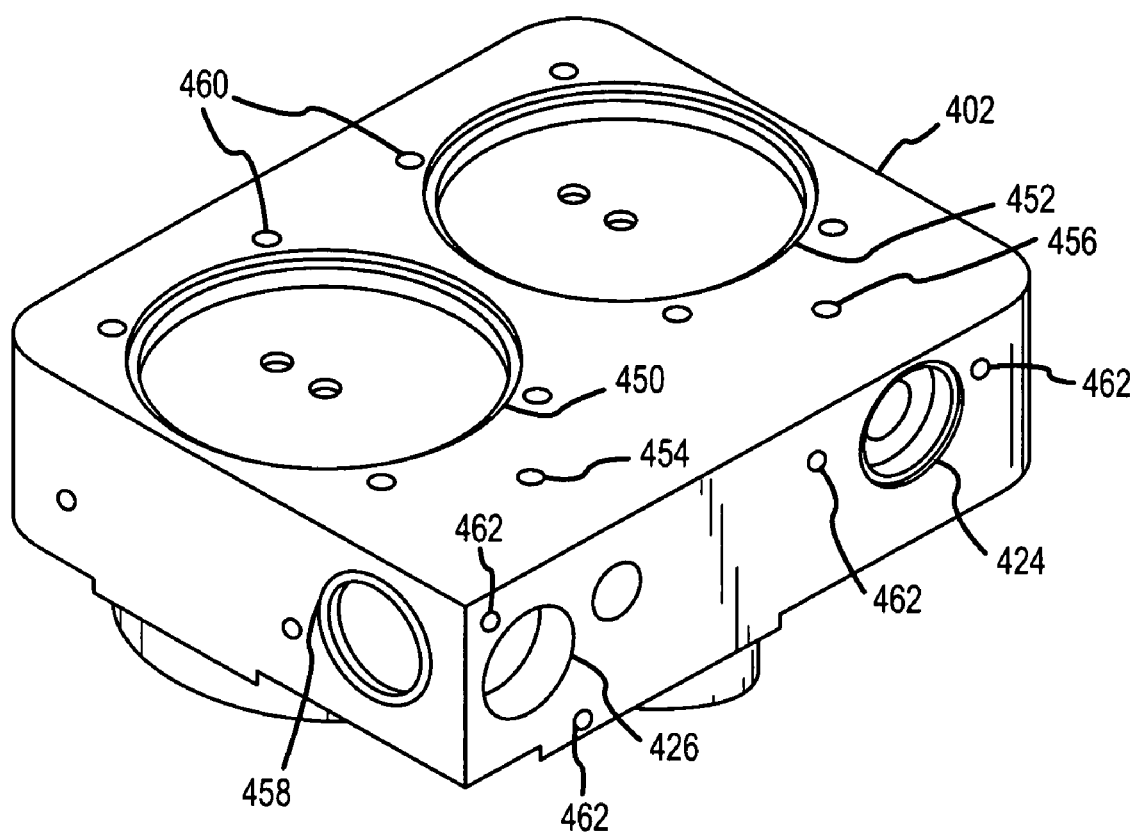
FIG. 4 is an isometric top view of manifold 402 in one example embodiment of the invention.

FIG. 4 is an isometric top view of manifold 402 in one example embodiment of the invention. Manifold 402 has integrated compressed air regulator mount 450 and integrated oxygen regulator mount 452 formed into the top surface of manifold 402. Four bolt holes 460 are used to attach each regulator to their respective integrated regulator mounts. Compressed air inlet opening 426 and oxygen inlet opening 424 are formed into the front face of manifold 402. Optional air pressure sensor mount 454 is formed into the top surface of manifold 402 and intersects with compressed air inlet opening 426. Optional oxygen pressure sensor mount 456 is formed into the top surface of manifold 402 and intersects with oxygen inlet opening 424. Shuttle plug access port 458 is formed into the side of manifold 402 and is used to insert a shuttle plug into a pneumatic shuttle valve formed inside manifold 402. Screw holes 462 are used to attach horse shoe clips (not shown) that hold a compressed air connector (not shown) and an oxygen connector (not shown) into compressed air inlet opening 426 and oxygen inlet opening 424. In one example embodiment of the invention, manifold 402 is fabricated from metal, for example Aluminum, stainless steal or the like. Other materials may also be used to form manifold 402, for example plastic, or a ceramic material.

Figure 5:
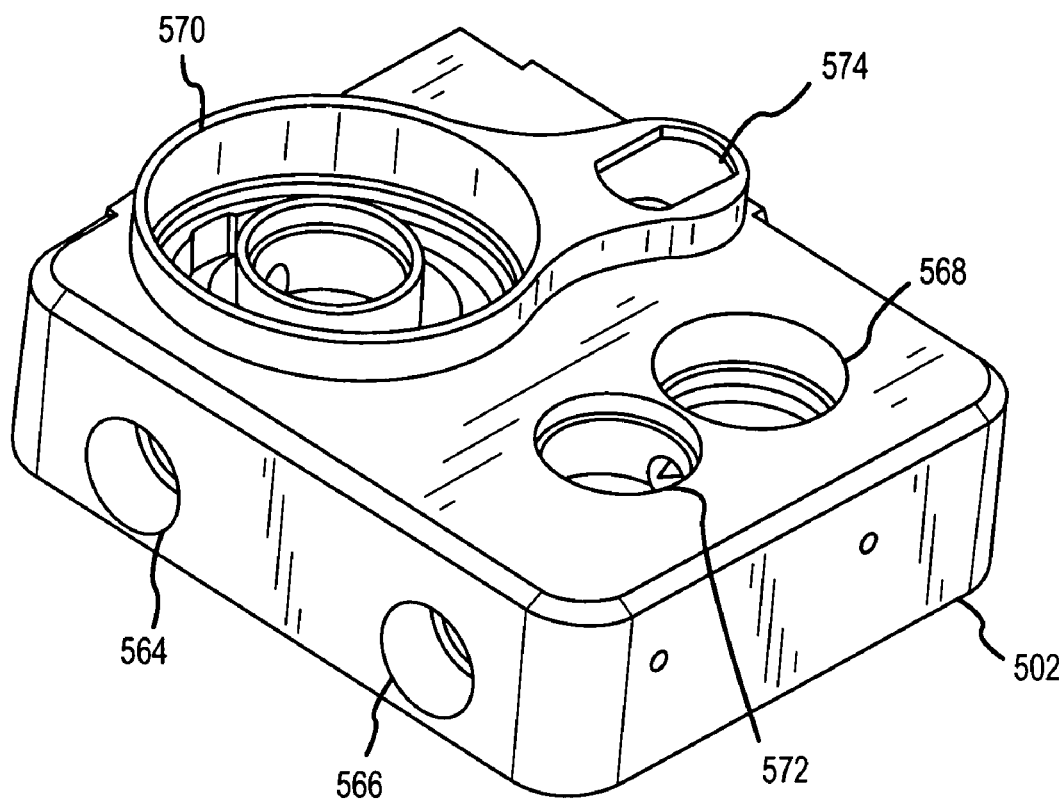
FIG. 5 is an isometric bottom view of manifold 502 in one example embodiment of the invention.

FIG. 5 is an isometric bottom view of manifold 502 in one example embodiment of the invention. Air outlet opening 564 and oxygen outlet opening 566 are formed into the back face of manifold 502. Integrated air filter mount 570 and integrated oxygen filter mount 568 are formed into the bottom side of manifold 502. Compressor inlet opening 574 is also formed into the bottom side of manifold 502. Oxygen regulator access port 572 is also formed into the bottom of manifold 502.

Figure 6:
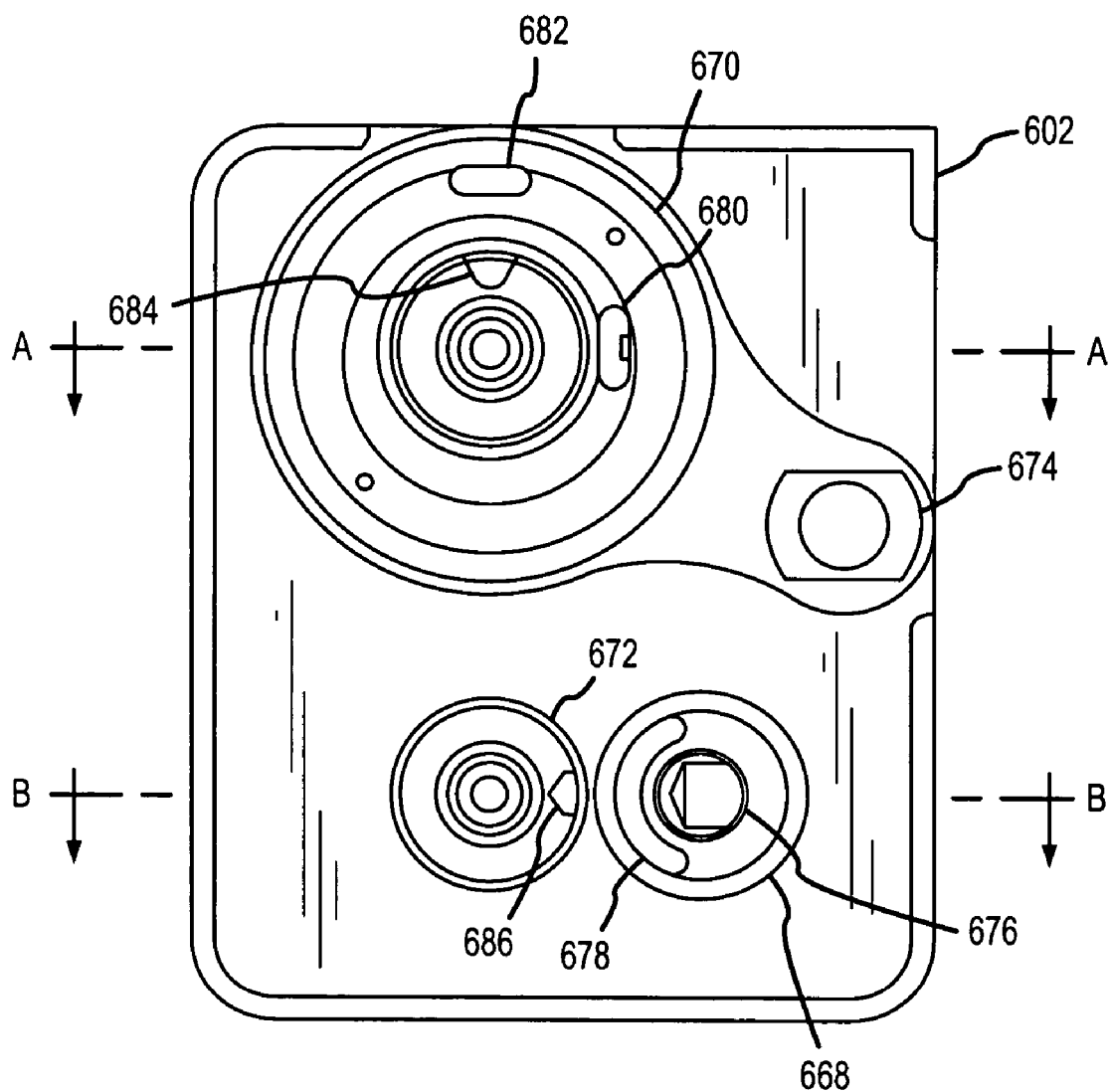
FIG. 6 is a bottom view of a drawing of manifold 602 in one example embodiment of the invention.

FIG. 6 is a bottom view of a drawing of manifold 602 in one example embodiment of the invention. Integrated air filter mount 670 and integrated oxygen filter mount 668 are formed into the bottom side of manifold 602. Compressor inlet opening 674 and oxygen regulator access port 672 are also formed into the bottom side of manifold 602. Oxygen filter inlet port 676 and oxygen filter outlet port 678 can be seen in integrated oxygen filter mount 668 formed in the bottom surface of manifold 602. Oxygen regulator inlet port 686 can be seen in oxygen regulator access port 672. Air filter inlet port 680, air filter outlet ports 682 and air regulator inlet port 684 can be seen in integrated air filter mount 670 formed into the bottom of manifold 602.

There may be two main flow paths in the manifold, one for oxygen and one for air. The oxygen flow path is shown in sectional view BB from FIG. 6. The air flow path is partially shown in sectional view AA from FIG. 6. The air flow path can not be fully shown in sectional view AA because the air flow path is more complex. The air flow path is more complex for a number of reasons. The first reason is that the compressed air source can be connected to the manifold in two different locations, at the compressed air inlet opening (not shown) on the front face of the manifold or at the compressor inlet opening 674 on the bottom side of the manifold. A pneumatic shuttle valve is built into the manifold that switches between the two potential connection points for the compressed air source. In addition, the air filter is much larger than the oxygen filter, so some of the gas passageways have been rotated 90 deg. to help limit the manifold to a given width.

Figure 7:
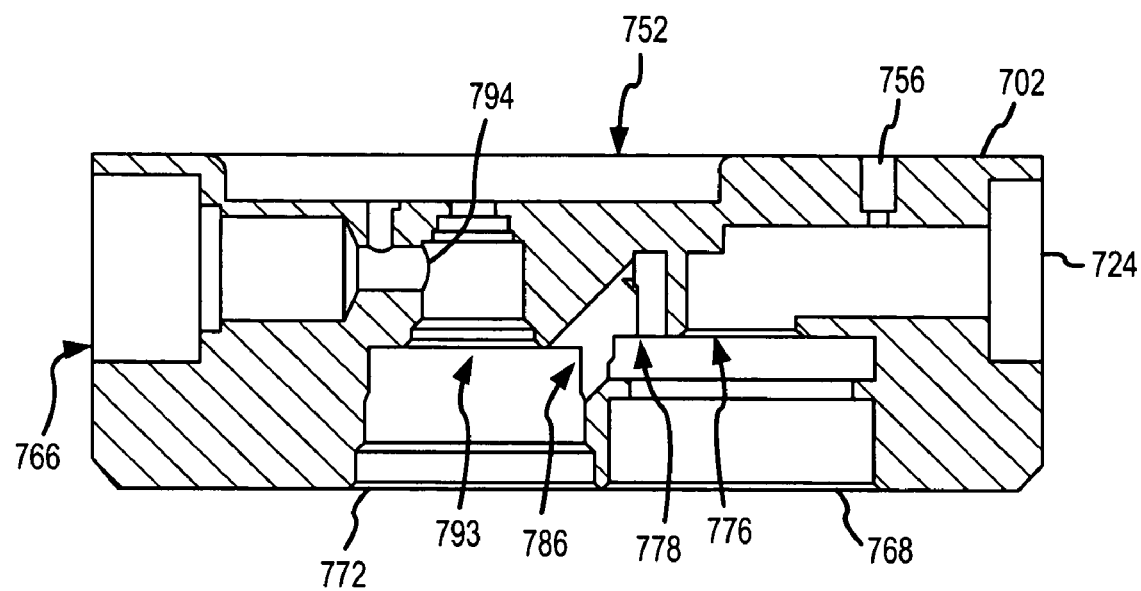
FIG. 7 is a sectional view of the oxygen flow path through manifold 702 in one example embodiment of the invention.

FIG. 7 is a sectional view of the oxygen flow path through manifold 702 in one example embodiment of the invention. FIG. 7 is from section BB of FIG. 6. Oxygen path starts at oxygen inlet opening 724 that forms a passageway connecting to oxygen filter inlet port 776 in integrated oxygen filter mount 768. Integrated oxygen filter mount 768 is formed into the bottom side of manifold 702. Oxygen filter outlet port 778 exits from integrated oxygen filter mount 768 and is connected to oxygen regulator inlet port 786 by a passageway formed in the side of oxygen access port 772. Oxygen then flows into oxygen regulator inlet port 793 and out of oxygen regulator outlet port 794. Oxygen regulator outlet port 794 is connected to Oxygen outlet port 766. An optional oxygen pressure sensor mount 756 can be formed into the top surface of manifold 702. The oxygen pressure sensor mount 756 is directly coupled to the oxygen inlet opening 724. Because of the direct coupling to the inlet opening, a pressure sensor mounted in this location may be more sensitive to changes in the oxygen inlet pressure.

Figure 8:
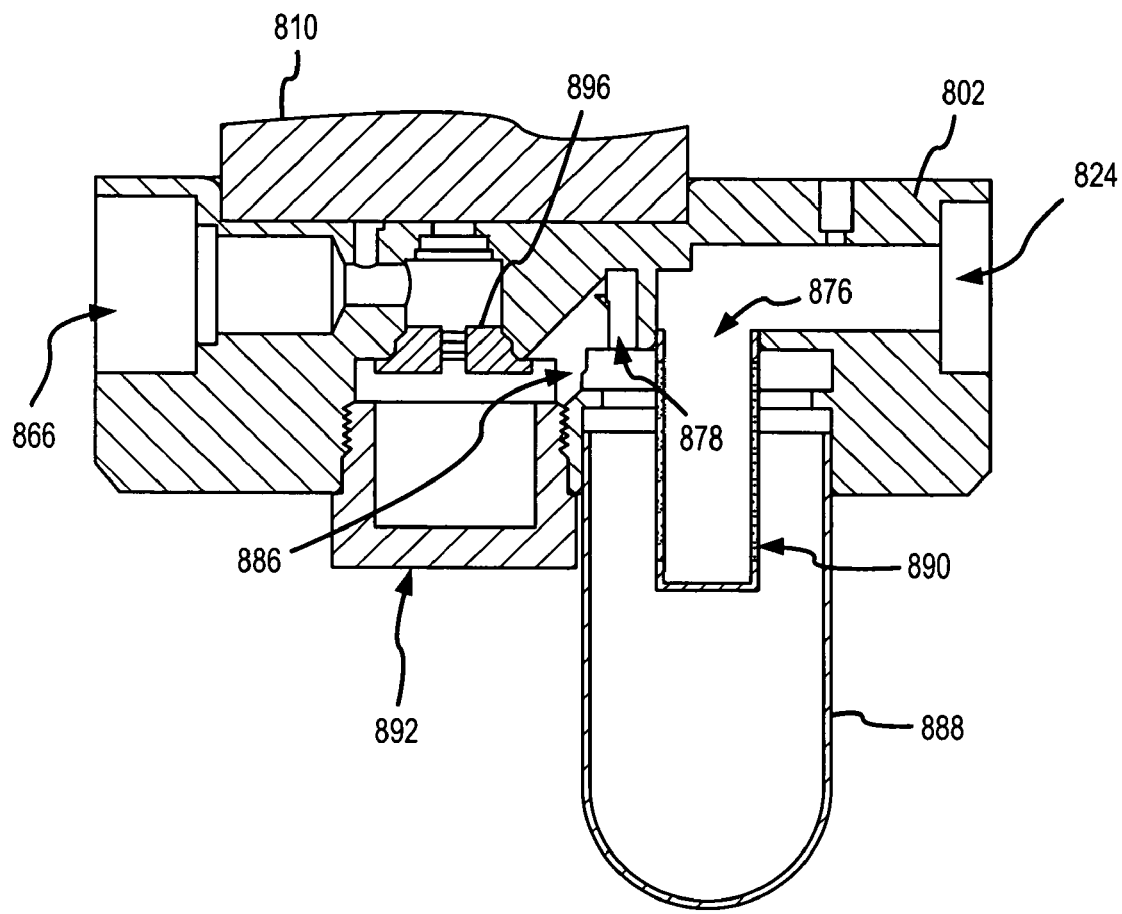
FIG. 8 is a sectional view of the oxygen flow pathway in a manifold assembly in one example embodiment of the invention.

FIG. 8 is a sectional view of the oxygen flow pathway in a manifold assembly in one example embodiment of the invention. The manifold assembly comprises manifold 802, oxygen filter element 890, oxygen filter bowl 888, valve spring retaining plug 892, valve seat 896, and oxygen regulator 810. Some parts in the manifold assembly have been removed for clarity, for example the valve assembly and valve spring.

In operation, oxygen enters the oxygen inlet opening 824 formed in manifold 802. The oxygen is forced through oxygen filter element 890 that is attached to oxygen filter inlet port 876. Oxygen filter bowl 888 forces the oxygen into oxygen filter outlet port 878. The oxygen then exits the oxygen regulator inlet port 886 and is forced by valve spring retaining plug 892 past oxygen valve seat 896 into oxygen outlet opening 866. Valve seat 896 is configured to mount directly into manifold 802. The interaction of oxygen regulator and valve spring/valve seat are well known in the art and are not shown to make the oxygen passageways in the manifold more visible. The oxygen filter element 890 that is used is typically a standard oxygen filter element.

Using this configuration for the oxygen path reduces the number of joints between the oxygen path and the outside air to 3 joints. The first joint is between the oxygen filter bowl and the manifold. The second joint is between the oxygen valve retainer plug and the manifold. The third joint is between the oxygen regulator and the manifold. An additional joint is created when optional oxygen pressure sensor mount is installed. By reducing the number of joints in the oxygen flow path, the potential for leaks has been reduced. The simplified oxygen flow path also reduced the pressure drop through the system.

Figure 9:
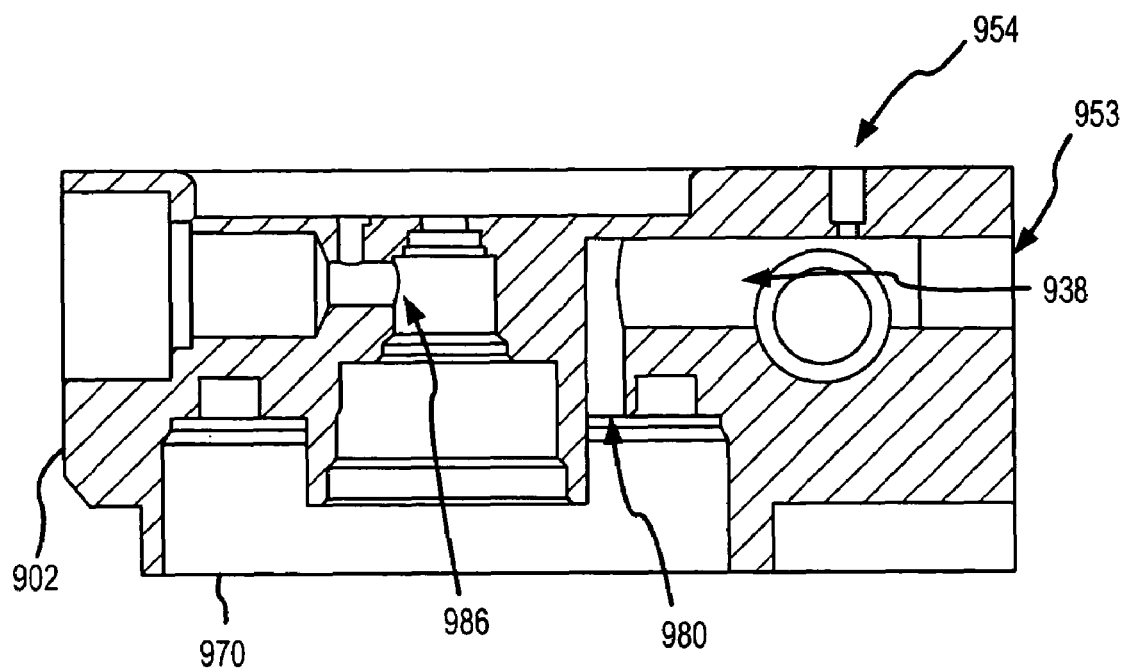
FIG. 9 is a sectional view of the air flow pathway through manifold 902 in one example embodiment of the invention.

FIG. 9 is a sectional view of the air flow path through manifold 902 in one example embodiment of the invention. FIG. 9 is from section AA of FIG. 6. In one example embodiment there may be two possible connections for the compressed air source. The compressed air source can be connected at a compressed air inlet opening or at a compressor inlet opening.(not shown). Both inlet openings lead to the exit port 938 of the pneumatic shuttle valve. When there are two sources, opening 953 is used for manufacturing access and is plugged during operation, typically with a ball bearing inserted into opening 953. When there is only one connection for the compressed air source, opening 953 would be the compressed air inlet opening. A passageway connects the exit port 938 to compressed air filter inlet port 980 in integrated compressed air filter mount 970. Integrated compressed air filter mount 970 is formed into the bottom side of manifold 902. The compressed air filter outlet port and the compressed air regulator inlet port have been rotated 90 degrees and are not in the plain cut by view AA, but can be seen in FIG. 6. Compressed air filter outlet port 682 exits from integrated compressed air filter mount 670 and is connected to compressed air regulator inlet port 684 by a passageway formed in compressed air filter mount 670. Compressed air flows into compressed air regulator inlet port 684 and out of compressed air regulator outlet port 986. Compressed air regulator outlet port 986 is connected to compressed air outlet port 982. Valve seat (not shown) is configured to mount directly into manifold 902. An optional compressed air pressure sensor mount 954 can be formed into the top surface of manifold 902. The compressed air pressure sensor mount 982 is directly coupled to the compressed air inlet opening. Because of the direct coupling to the inlet opening, a pressure sensor mounted in this location may be more sensitive to changes in the compressed air inlet pressure.

Figure 10:
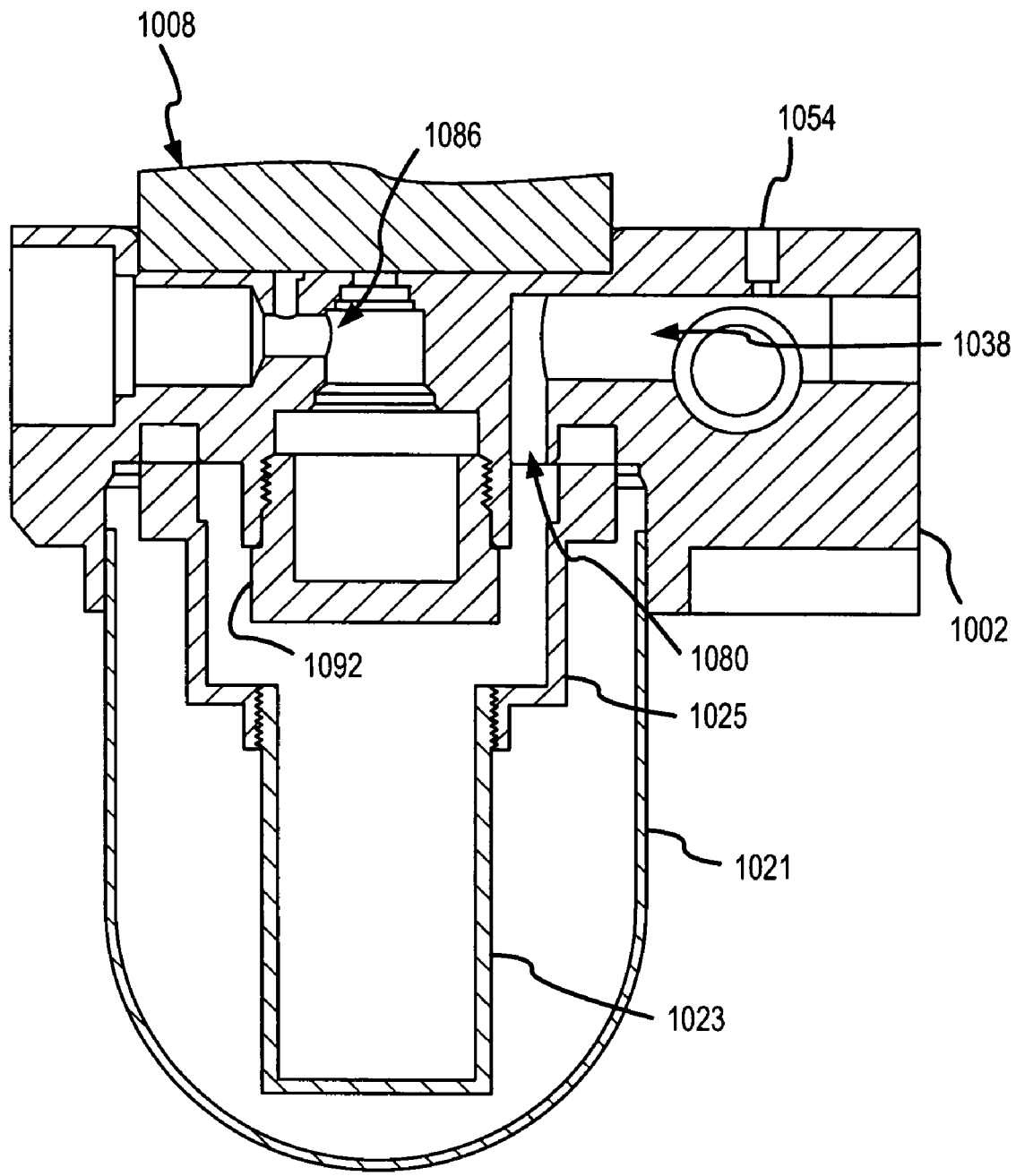
FIG. 10 is a sectional view of the compressed air pathway in a manifold assembly in one example embodiment of the invention.
Figure 11:
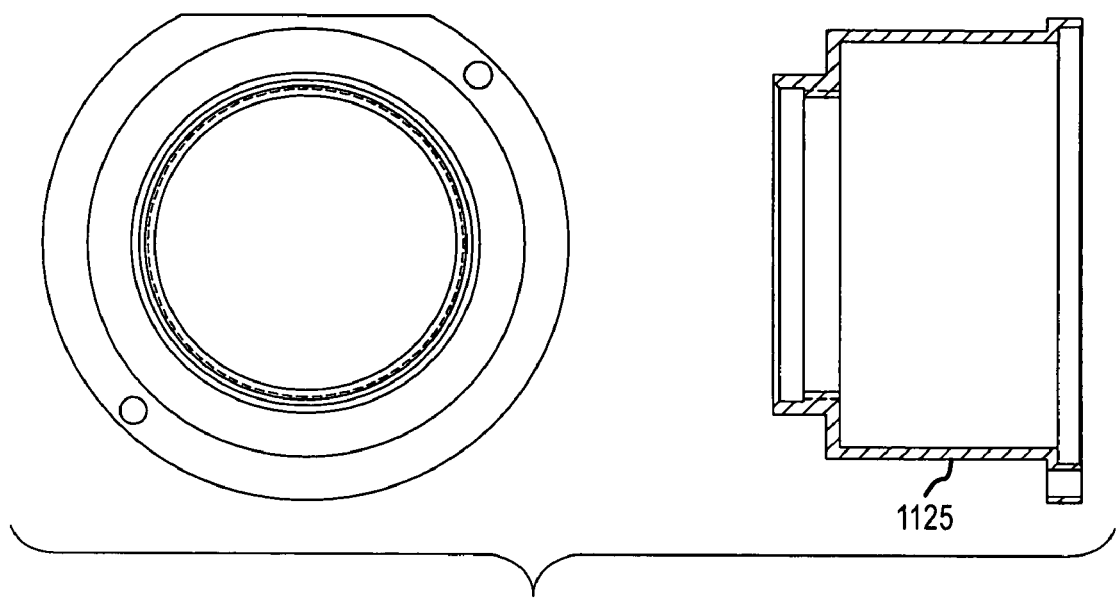
FIG. 11 is a drawing of a compressed air filter adapter in one example embodiment of the invention.
Figure 12:
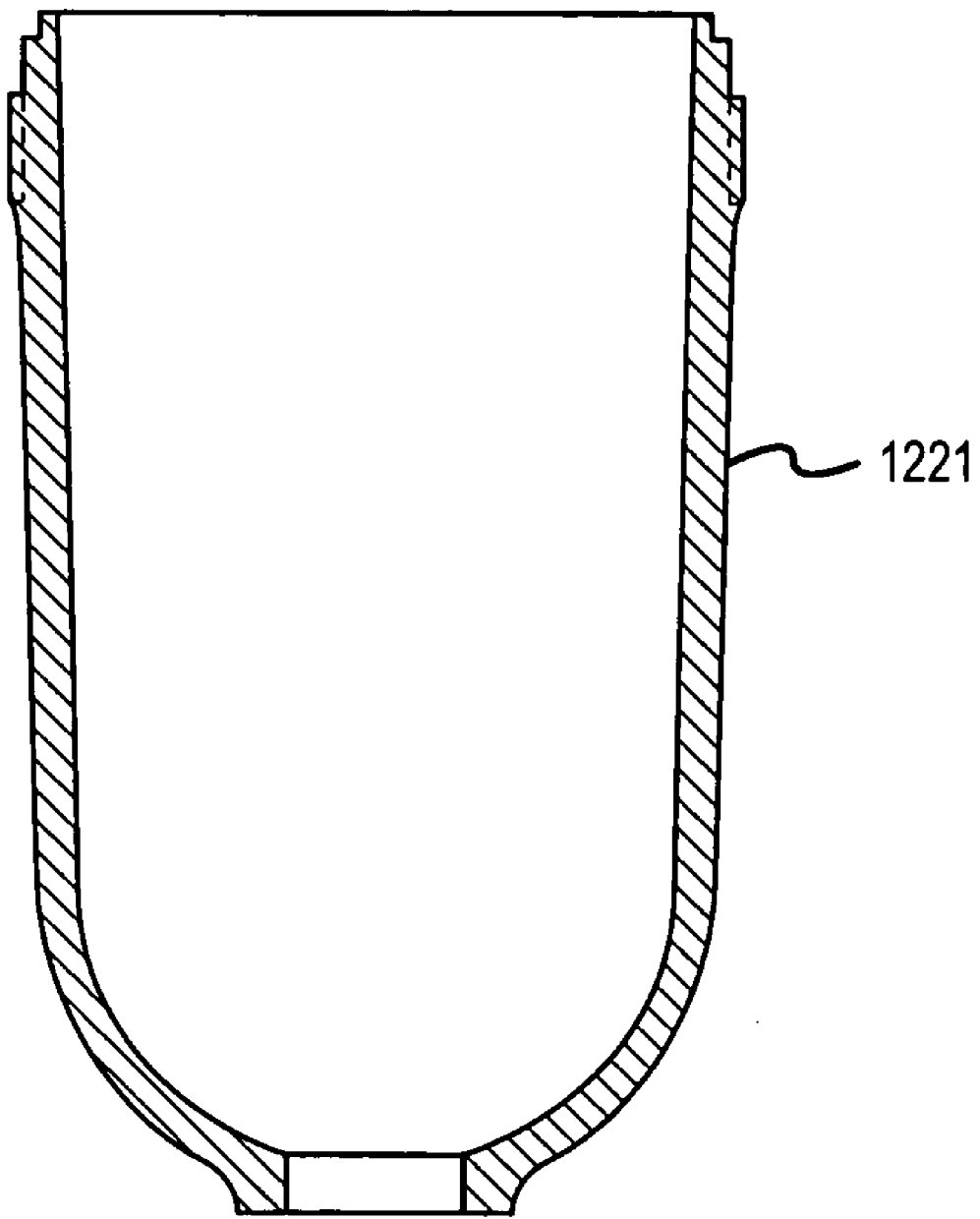
FIG. 12 is a drawing of a compressed air filter bowl in one example embodiment of the invention.

FIG. 10 is a sectional view of the compressed air pathway in a manifold assembly in one example embodiment of the invention. Manifold assembly comprises manifold 1002, compressed air filter bowl 1021, compressed air filter element 1023, compressed air filter adapter 1025, valve spring retaining plug 1092, and compressed air regulator 1008. FIG. 11 is a drawing of compressed air filter adapter 1125 in one example embodiment of the invention. FIG. 12 is a drawing of compressed air filter bowl 1221 in one example embodiment of the invention. Some parts in the manifold assembly have been removed for clarity, for example the air valve assembly, air valve seat and air valve spring.

In operation, compressed air enters one of the compressed air inlet opening (not shown) formed in manifold 1002. The pneumatic shuttle valve (not shown) forces the air into shuttle valve exit port 1038 and enters the inlet port of the compressed air filter mount 1080. The compressed air is forced through compressed air filter element 1023 that is attached to compressed air filter adaptor 1025. Compressed air filter bowl 1021 forces the compressed air into compressed air filter outlet port 682. The compressed air then exits the compressed air regulator inlet port 684 and is forced by valve spring retaining plug 1092 into compressed air outlet opening 1086. The interaction of compressed air regulator and valve spring/valve seat are well known in the art and are not shown to make the compressed air passageways in the manifold more visible. The compressed air filter element 1023 that is used is typically a standard compressed air filter element.

Using this configuration for the compressed air path reduces the number of joints between the compressed air path and the outside air to 2 joints. The first joint is between the compressed air filter bowl and the manifold. The second joint is between the compressed air regulator and the manifold. An additional joint is created when optional compressed air pressure sensor mount is installed. By reducing the number of joints in the compressed air flow path, the potential for leaks has been reduced. The simplified compressed air flow path also reduced the pressure drop through the system.

Figure 13:
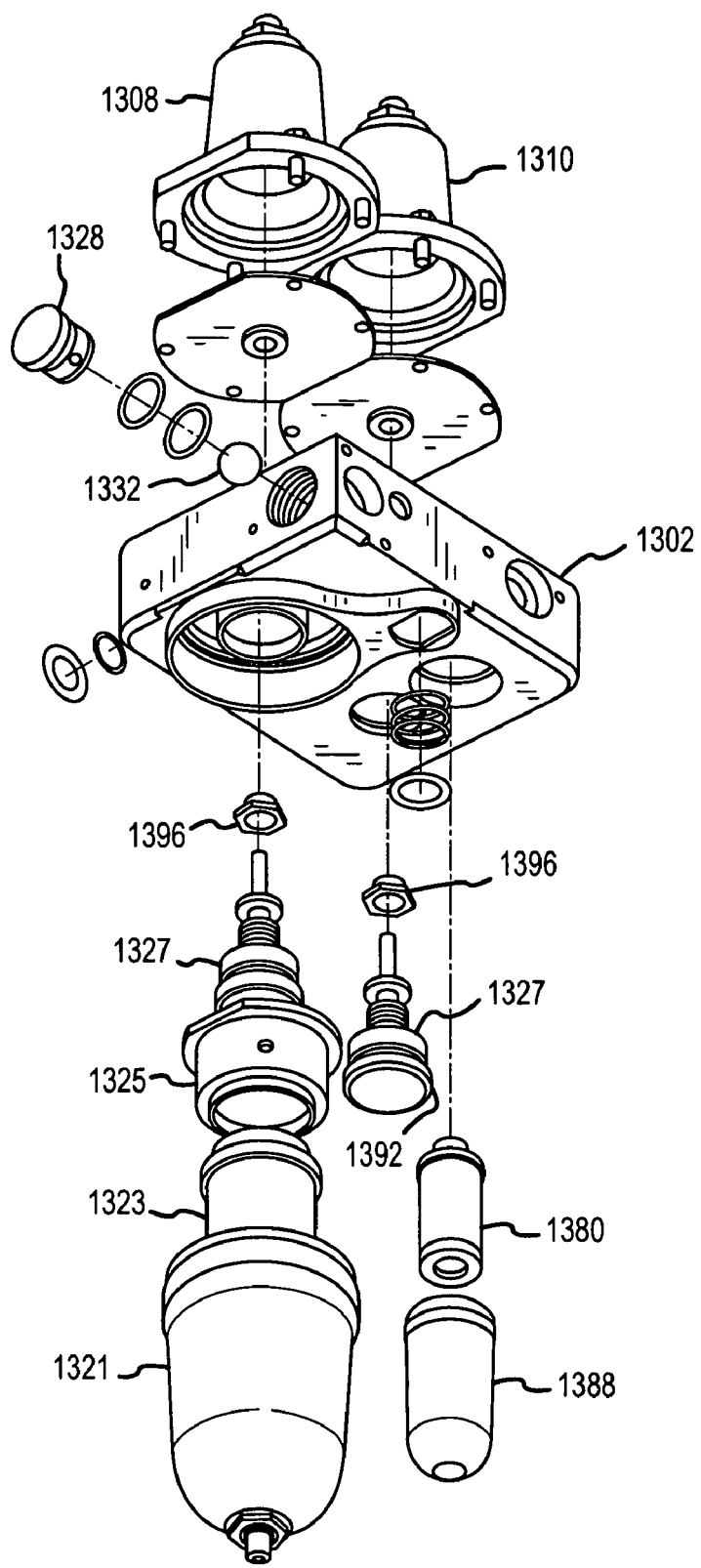
FIG. 13 is an exploded view of a manifold assembly in one example embodiment of the invention.

FIG. 13 is an exploded view of a manifold assembly in one example embodiment of the invention. Manifold assembly comprises: manifold 1302, oxygen regulator case 1310, compressed air regulator case 1308, shuttle plug 1332, shuttle plug cap 1328, two valve seats 1396, two valve spring assemblies 1327, two valve spring retaining plugs 1392, air filter adaptor 1325, air filter element 1323, air filter bowl assembly 1321, oxygen filter bowl 1388, and oxygen filter element 1390. Air filter bowl assembly comprise air filter bowl and a drain valve mounted in the bottom surface of the air filter bowl. The two valve seats mount directly into their respective regulator mounts formed into the manifold 1302. The two valve spring assemblies are held against, and interact with, the valve seats, by the two valve spring retaining plugs.

Figure 20:
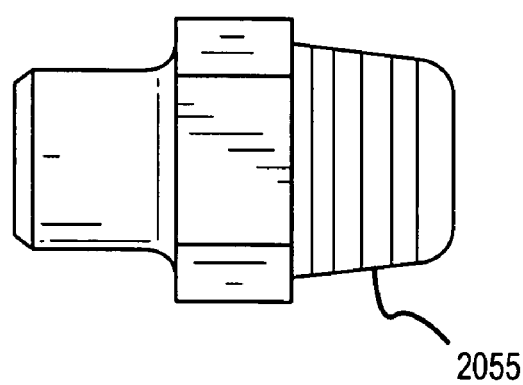
FIG. 20 is a drawing of Pneufit self sealing connector 2055 in one example embodiment of the invention.

In prior art air filter bowl assemblies, the drain valve was a manual valve. To drain accumulated liquid using a manual drain valve the user would have to hold a cup or bucket underneath the air filter assembly while trying to open the drain valve. This was awkward at best and could cause the liquid to spill or spray onto the user. In one example embodiment of the current invention, a Pneufit self sealing connector is used in the bottom of the air filter assembly, for example the self sealing connector made by Norgren, part number 12 424 0418. With this fixture installed in the filter bowl, to drain accumulated liquid the user just inserts a tube into the end of the fitting. The tube compresses a spring and unseats a plunger, allowing the fluid to drain through the inserted tube. One end of the tube may be already inserted into a bucket or drain. Once the fluid has been removed, the user may remove the tubing, allowing the plunger to reseat and reseal the drain fixture. FIG. 20 is a drawing of Pneufit self sealing connector 2055 in one example embodiment of the invention. Self-sealing connectors may also be known as quick-action couplers, single-poppet connector, or self-sealing couplers.

Figure 14:
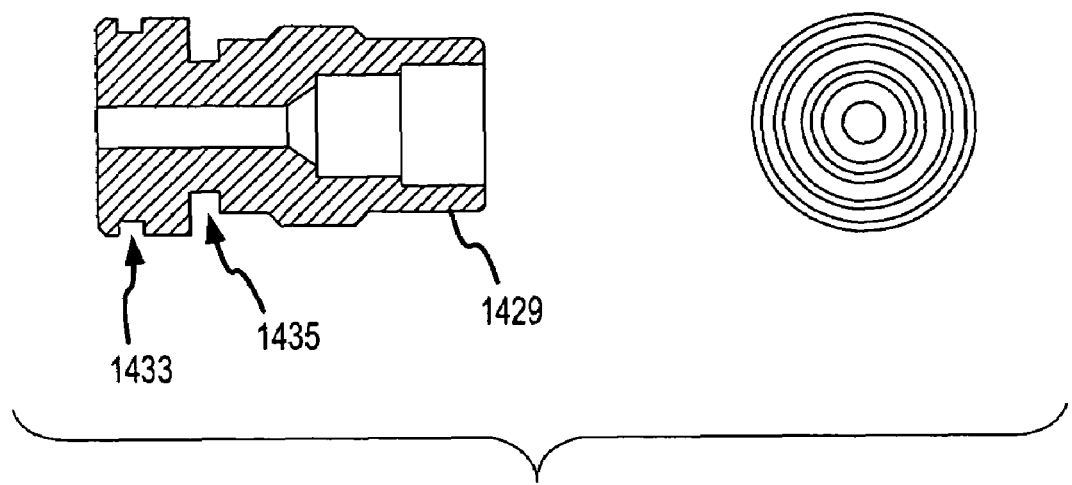
FIG. 14 is a drawing of an air fitting in one example embodiment of the invention.
Figure 15:
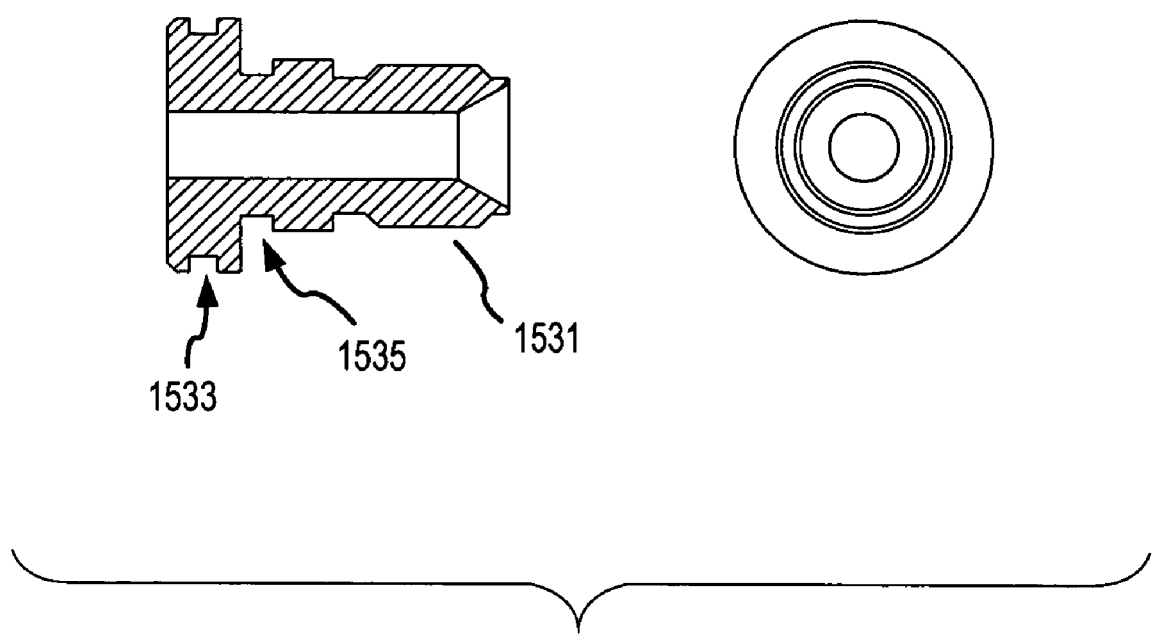
FIG. 15 is a drawing of an oxygen fitting in one example embodiment of the invention.

A compressed air inlet fitting and an oxygen inlet fitting are attached to a manifold by two horse shoe clips in one example embodiment of the invention. FIG. 14 is a drawing of a compressed air inlet fitting in one example embodiment of the invention. FIG. 14 shows compressed air inlet fitting 1429 with O-ring groove 1433 and horse shoe groove 1435. FIG. 15 is a drawing of an oxygen inlet fitting in one example embodiment of the invention. FIG. 15 shows oxygen inlet fitting 1531 with O-ring groove 1533 and horse shoe groove 1535. In one example embodiment of the invention, oxygen inlet fitting 1531 and compressed air inlet fitting 1429 are configured to be incompatible such that the oxygen source can not be connected to the compressed air inlet fitting 1429 and the compressed air source can not be connected to the oxygen inlet fitting 1531. In addition, the outer diameter of the fittings and the inlet openings in the manifold that the fittings mates with, may be sized differently for the two fittings. In one example embodiment of the invention the air inlet fitting may have an outer diameter of 0.816 inches and the air inlet opening in the manifold may be 0.820 inches in diameter, where the oxygen inlet fitting may have a diameter of 0.881 inches and the oxygen inlet opening in the manifold may be 0.866 inches in diameter. This prevents the oxygen inlet fitting from being installed in the compressed air inlet opening of the manifold. By making the outer diameter and mating holes different sizes for the two fittings and making the fittings incompatible, the oxygen source and the air source are more likely to be connected to the correct place in the ventilator system. Other design choices can be made to prevent the oxygen inlet fixture from being installed in the incorrect inlet opening. For example, the size or shape may be different between the two inlet openings and their corresponding inlet fittings, or a key feature may be added to one of the inlet fittings and the corresponding inlet opening. A key feature is typically one or more features that prevent the insertion of a mating part that does not contain the corresponding features, for example a slot with a matching protrusion.

A filter disk, for example a filter disk having openings 40 microns in size, may be inserted into the oxygen inlet opening. The filter disk would be held inside the oxygen inlet opening by the oxygen inlet fitting. In one example embodiment of the invention, a spring may be inserted with the filter disk to force the filter disk against the manifold. The filter disk may prevent contamination from entering the manifold when an oxygen source is not coupled to the oxygen inlet fitting.

Figure 16:
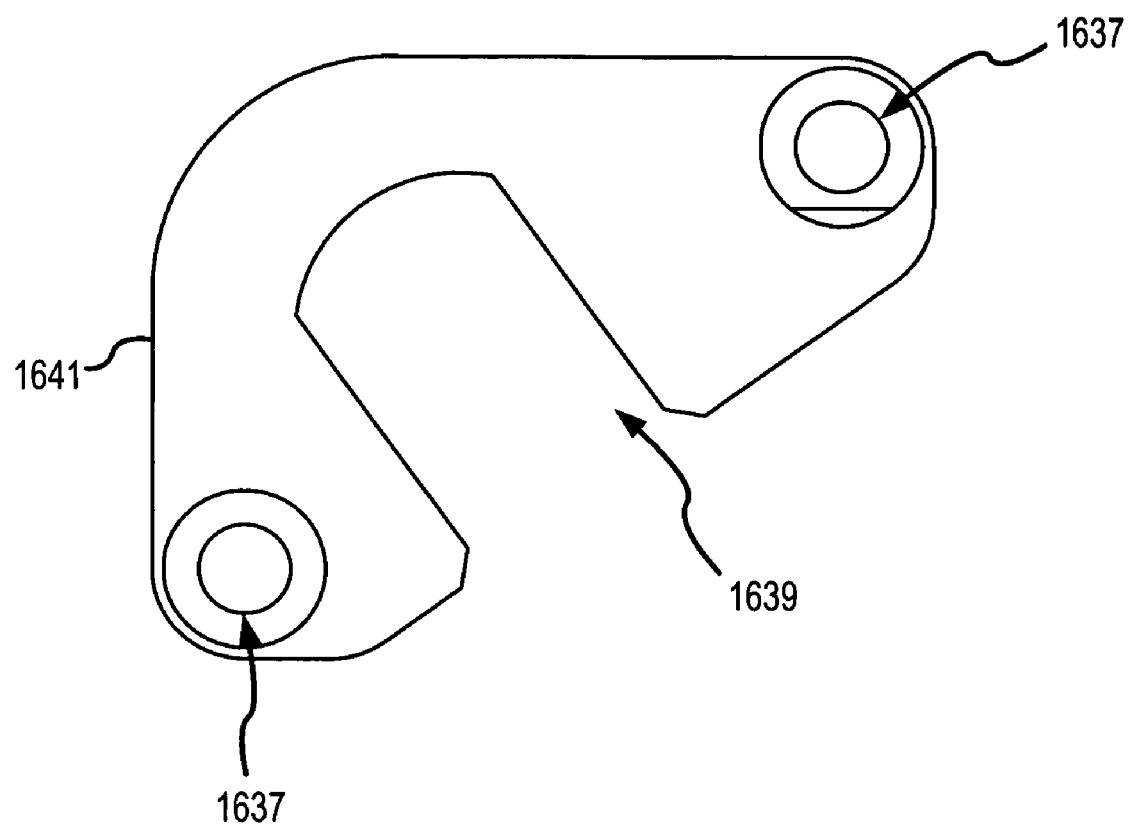
FIG. 16 is a drawing of a horse shoe clip in one example embodiment of the invention.

FIG. 16 is a drawing of a horse shoe clip in one example embodiment of the invention. Horse shoe clip 1642 has two screw holes 1637 and retaining feature 1639. In operation, O-rings are installed into the two O-ring grooves on the oxygen and air fittings. The retaining feature 1639 of two horse shoe clips mates with the horse shoe groove (1535 and 1435) in air fitting 1429 and in oxygen fitting 1531. Screws inserted through screw holes 1637 hold horse shoe clip onto manifold, thereby securing the air and oxygen fittings into their respective inlet ports in the manifold.

Figure 17:
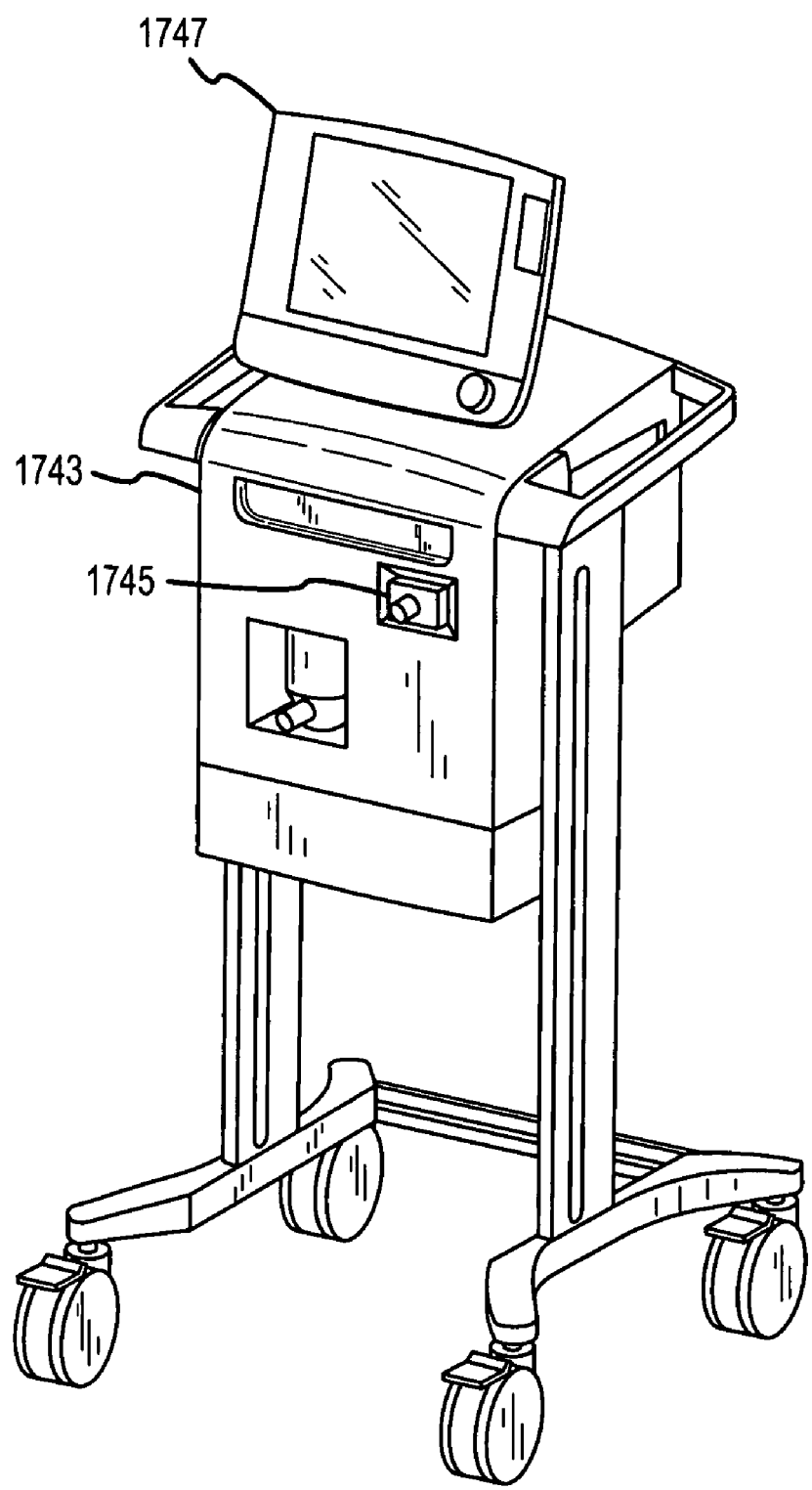
FIG. 17 is an isometric front view of a ventilator system in an example embodiment of the invention.
Figure 18:
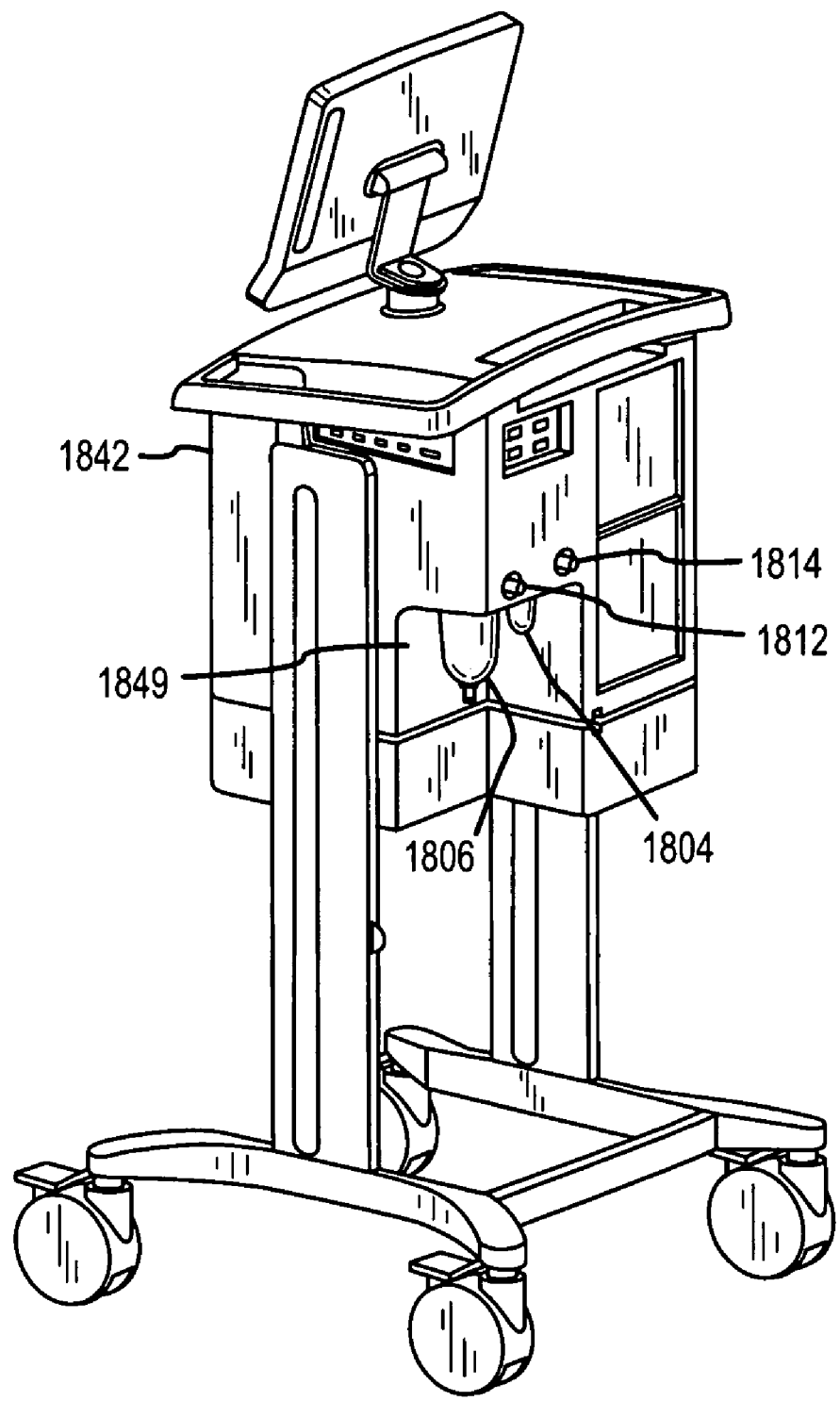
FIG. 18 is an isometric back view of a ventilator system in an example embodiment of the invention.

FIG. 17 is an isometric front view of a ventilator system in an example embodiment of the invention. Ventilator system 1743 has display 1747 and gas outlet port 1745. FIG. 18 is an isometric back view of a ventilator system in an example embodiment of the invention. Ventilator system 1842 has a cutout region 1849. Oxygen filter 1804 and air filter 1806 extend down into cutout region 1849, allowing easy access to the two filters. Cutout region allows the oxygen and compressed air filters to be exposed for easy access by a user. This allows a user to change the filter elements in the filters, or drain any accumulated liquid in the air filter, without having to open a panel in the ventilator system. Oxygen inlet fitting 1814 and air inlet fitting 1812 are located on the back face of ventilator system 1842, allowing easy access to the two inlet fittings. In one example embodiment of the invention, a manifold assembly is hidden inside the ventilator system just above cutout region 1849 and includes oxygen inlet fitting 1814, air inlet fitting 1812, oxygen filter 1804 and air filter 1806.

I claim:

1. A manifold assembly, comprising:
 a manifold having a first face and a second face opposite the first face;
 a first diaphragm assembly and regulator case of a first regulator mounted to a first side of a first regulator mount formed into the first face;
 a second side of the first regulator mount formed into the second face;
 a first gas passageway coupling the first side of the first regulator mount with the second side of the first regulator mount;
 a first valve seat mounted into the second side of the first regulator mount and coupled to the first gas passageway, the first valve seat having a top side and a bottom side where the top side is towards the first face of the manifold;
 a first valve spring retaining plug mounted into the second side of the first regulator mount where the first valve spring retaining plug holds a first valve spring assembly against the bottom side of the first valve seat;
 a first gas inlet port coupled to the first gas passageway between the bottom side of the first valve seat and the first valve spring retaining plug;
 a first gas outlet port coupled to the first gas passageway above the top side of the first valve seat.

2. The manifold assembly of claim 1 where the manifold assembly is integrated into a ventilator.

3. The manifold assembly of claim 1 where the first regulator is for regulating an output pressure of oxygen.

4. The manifold assembly of claim 1 further comprising:
 a second diaphragm assembly and regulator ease of a second regulator mounted to a first side of a second regulator mount formed into the first face;
 a second side of the second regulator mount formed into the second face;
 a second gas passageway coupling the first side of the second regulator mount with the second side of the second regulator mount;
 a second valve seat mounted into the second side of the second regulator mount and coupled to the second gas passageway, the second valve seat having a top side and a bottom side where the top side is towards the first face of the manifold;
 a second valve spring retaining plug mounted into the second side of the second regulator mount where the second valve spring retaining plug holds a second valve spring assembly against the bottom side of the second valve seat;
 a second gas inlet port coupled to the second gas passageway between the bottom side of the second valve seat and the second valve spring retaining plug;
 a second gas outlet port coupled to the second gas passageway above the top side of the second valve seat.

5. The manifold assembly of claim 4 where the second regulator is for regulating an output pressure of compressed air.

6. The manifold assembly of claim 4 further comprising:
 a filter mount formed into the second side of the manifold where the filter mount is centered on the first regulator mount and an outlet port of the filter mount is coupled to the second gas inlet port.

\* \* \* \* \*